| United States Patent [19] | [11] Patent Number: 5,023,277 |
|---|---|
| McAteer | [45] Date of Patent: Jun. 11, 1991 |

[54] SYNGAS CONVERSION CATALYST ITS PRODUCTION AND USE THEREOF

[75] Inventor: Colin H. McAteer, Aldershot, England

[73] Assignee: The British Petroleum Company p.l.c., London, England

[21] Appl. No.: 549,631

[22] Filed: Jul. 6, 1990

Related U.S. Application Data

[63] Continuation of Ser. No. 282,213, Dec. 9, 1988, abandoned, which is a continuation-in-part of Ser. No. 97,807, Sep. 16, 1987, Pat. No. 4,826,800.

[30] Foreign Application Priority Data

Sep. 26, 1986 [GB] United Kingdom ............... 8623233

[51] Int. Cl.$^5$ .............................................. C07C 1/04
[52] U.S. Cl. .................................. 518/715; 518/700; 518/714; 545/310; 545/319
[58] Field of Search .................. 518/715, 700, 714; 585/310, 319

[56] References Cited

U.S. PATENT DOCUMENTS

| 2,548,159 | 4/1951 | Houtman et al. ............... 518/715 |
| 2,850,515 | 9/1958 | Riblett et al. .................. 518/715 |
| 4,039,302 | 8/1977 | Khera II . | |
| 4,088,671 | 5/1978 | Kobylinski ................... 518/715 |
| 4,107,091 | 8/1978 | Khera I . | |
| 4,410,637 | 10/1983 | Kortbeek et al. ............. 518/715 |
| 4,423,265 | 12/1983 | Chu et al. ..................... 518/700 |
| 4,500,417 | 2/1985 | Chen et al. ................... 208/950 |
| 4,520,215 | 5/1985 | Owen et al. .................. 585/533 |
| 4,544,792 | 10/1985 | Smith et al. ................. 585/533 |
| 4,595,703 | 6/1986 | Payne et al. ................. 518/715 |
| 4,599,481 | 7/1986 | Post et al. .................... 518/715 |

FOREIGN PATENT DOCUMENTS 2021145 11/1979 United Kingdom .
2146350 4/1985 United Kingdom .

OTHER PUBLICATIONS

Sapienza et al., "Catalysts for the Production of Hydrocarbons from Carbon Monoxide and Water", U.S. Statutory Invention Registration No. H243, published Apr. 7, 1987, Filed Nov. 6, 1985.

*Primary Examiner*—Howard T. Mars
*Attorney, Agent, or Firm*—Brooks Haidt Haffner & Delahunty

[57] ABSTRACT

A composition for use after reductive activation as a catalyst in the conversion of synthesis gas to hydrocarbons, which composition comprises as essential components (i) cobalt either as the elemental metal, the oxide or a compound thermally decomposable to the elemental metal and/or oxide and (ii) zinc in the form of the oxide or a compound thermally decomposable to the oxide.

5 Claims, No Drawings

SYNGAS CONVERSION CATALYST ITS PRODUCTION AND USE THEREOF

This application is a continuation of application Ser. No. 07/282,213 filed Dec. 9, 1988 and now abandoned which in turn is a continuation-in-part of application Ser. No. 07/097,807, filed Sept. 16, 1987, now U.S. Pat. No. 4,826,800 claiming priority from British application No. 8623233, filed Sept. 26, 1986. The subject matter claimed herein has an effective filing date of Sept. 26, 1986.

The present invention relates to a composition for use after reductive activation as a catalyst in the conversion of gaseous mixtures principally comprising carbon monoxide and hydrogen, hereinafter to be referred to as synthesis gas, to hydrocarbons, in particular to hydrocarbons in the $C_5$–$C_{60}$ range, to processes for producing the catalyst and to a process utilising the catalyst in the conversion of synthesis gas to the aforesaid hydrocarbons.

The conversion of sythesis gas into hydrocarbons by the Fischer-Tropsch ("FT") process has been known for many years but the process has only achieved commercial significance in countries such as South Africa where unique economic factors prevail. The growing importance of alternative energy sources such as coal and natural gas has focussed renewed interest in the Fischer-Tropsch process as one of the more attractive direct and environmentally acceptable routes to high quality transportation fuels.

Many metals, for example cobalt, nickel, iron, molybdenum, tungsten, thorium, ruthenium, rhenium and platinum are known to be catalytically active, either alone or in combination, in the conversion of synthesis gas into hydrocarbons and oxygenated derivatives thereof. Of the aforesaid metals, cobalt, nickel and iron have been studied most extensively. Generally, the metals are used in combination with a support material, of which the most common are alumina, silica and carbon.

The use of cobalt as a catalytically active metal in combination with a support has been described in, for example, EP-A-127220, EP-A-142887, GB-A-2146350, GB-A-2130113 and GB-A-2125062. EP-A-127220, for example, discloses the use of a catalyst comprising (i) 3–60 pbw cobalt, (ii) 0.1–100 pbw zirconium, titanium, ruthenium or chromium, per 100 pbw silica, alumina or silica-alumina, (iii) the catalyst having been prepared by kneading and/or impregnation.

Our own published European application No. 0209980 (BP Case No. 6131) describes the use in the conversion of synthesis gas to hydrocarbons of a catalyst having a composition represented by the formula:

$$Co_a A_b La_c CeO_x$$

wherein
A is an alkali metal
a is greater than zero and up to 25% w/w,
b is in the range from zero to 5% w/w,
c is in the range from zero to 15% w/w,
x is a number such that the valence requirements of the other elements for oxygen is satisfied, and the remainder of the composition, subject to the requirement for x, is cerium,
the percentages w/w being based on the total weight of the composition.

We have now found that compositions containing cobalt and zinc oxide as essential components are, after reductive activation, active as catalysts in the conversion of synthesis gas to hydrocarbons. Moreover, in contrast to many prior art cobalt-containing catalysts, as typified by the aforesaid European application publication No. 0209980, such catalysts are more selective to hydrocarbons in the $C_5$–$C_{60}$ range and, in fact can be very selective to a waxy hydrocarbon product.

Accordingly, the present invention provides a composition for use after reductive activation as a catalyst in the conversion of synthesis gas to hydrocarbons, which composition comprises as essential components (i) cobalt either as the elemental metal, the oxide or a compound thermally decomposable to the elemental metal and/or oxide and (ii) zinc in the form of the oxide or a compound thermally decomposable to the oxide.

Suitably the composition may contain up to 70%, preferably up to 40% cobalt, the remainder of the composition being zinc and oxygen, the percentages being based on an atomic basis.

The composition may also contain in elemental or oxide form one or more of the metals (M) chromium, nickel, iron, molybdenum, tungsten, zirconium, gallium, thorium, lanthanum, cerium, ruthenium, rhenium, palladium or platiunum, suitably in an amount up to 15% w/w.

Useful compositions, after thermal decomposition may suitably be represented by the formula:

$$Co_a M_b Zn_c O_x \qquad (I)$$

wherein
M is as above,
a is greater than zero and up to 70% w/w,
b is from zero to 15% w/w,
c is greater than zero, and
x is a number such that the valence requirements of the other elements for oxygen is satisfied.

The composition may suitably be unsupported or supported, suitably on a conventional refractory support material, for example silica, alumina, silica/alumina, zirconia, titania, or the like.

The composition may be prepared by a variety of methods including impregnation, precipitation or gelation. A suitable method, for example, comprises impregnating zinc oxide with a compound of cobalt thermally decomposable to the oxide. Any suitable impregnation technique including the incipient wetness technique or the excess solution technique, both of which are well-known in the art, may be employed. The incipient wetness technique is so-called because it requires that the volume of impregnating solution be predetermined so as to provide the minimum volume of solution necessary to just wet the entire surface of the support, with no excess liquid. The excess solution technique as the name implies, requires an excess of the impregnating solution, the solvent being thereafter removed, usually by evaporation.

The impregnation solution may suitably be either an aqueous solution or a nonaqueous, organic solution of the thermally decomposable cobalt compound. Suitable nonaqueous organic solvents include, for example, alcohols, ketones, liquid paraffinic hydrocarbons and ethers. Alternatively, aqueous organic solutions, for example an aqueous alcoholic solution, of the thermally decomposable cobalt compound may be employed.

Suitable soluble compounds include for example the nitrate, acetate or acetylacetonate, preferably the nitrate. It is preferred to avoid the use of the halides because these have been found to be detrimental.

It is preferred to produce the composition by precipitation, either by coprecipitation of the metals cobalt and zinc in the form of insoluble thermally decomposable compounds thereof or by precipitation of an insoluble thermally decomposable compound of cobalt in the presence of zinc oxide.

A particularly preferred process for producing a composition comprises the steps of:

(I) precipitating at a temperature in the range from 0° to 100° C. the metals cobalt and zinc in the form of insoluble thermally decomposable compounds thereof using a precipitant comprising ammonium hydroxide, ammonium carbonate, ammonium bicarbonate, a tetraalkylammonium hydroxide or an organic amine, and (II) recovering the precipitate obtained in step (I).

Step I of the aforesaid process may be accomplished in a variety of ways, some being better than others in terms of the activity of the final catalyst. Thus, an embodiment (A) comprises bringing together in solution at a temperature below 50° C. soluble salts of the metals cobalt and zinc and a precipitant comprising ammonium hydroxide, carbonate, or bicarbonate, a tetralkylammonium hydroxide or an organic amine. Alternatively, an embodiment (B) comprises bringing together in a substantially cobalt-free solution a soluble zinc salt with a precipitant so as to precipitate a zinc compound and thereafter in the presence of the precipitated zinc compound bringing together a solution of a soluble cobalt salt with a precipitant so as to precipitate an insoluble thermally decomposable cobalt compound. After precipitation of the zinc compound, the solution of the soluble cobalt salt may suitably be added to the precipitated zinc compound without any intervening treatment, such as for example filtration, prior to precipitating the cobalt compound. Alternatively, the precipitated zinc compound may be separated, washed and re-dispersed prior to precipitating the cobalt compound. Many variants on the aforesaid embodiments (A) and (B) are possible, for example instead of adding the precipitant to the salts, the salts may be added to the precipitant.

Addition of the precipitant causes the initially low pH of the mixture to rise. It is desirable in the preparation of catalysts according to the invention that the final pH of the mixture is greater than 6, preferably in the range from 7 to 10. The precipitant may be added until a pH in the aforesaid range is achieved, whereupon the addition of further precipitant may be discontinued, thereby arresting the rise in the pH. In order to improve the homogeneity of the catalyst it is preferred to agitate the mixture during precipitation, suitably by mechanical stirring.

In a particularly preferred alternative process for the production of a composition of the formula (I) steps (I) and (II) of the aforesaid process are replaced by the steps (I') and (II') as follows:

(I') bringing together in solution at a temperature below the boiling point of the solution soluble compounds of cobalt and zinc and a precipitant comprising either ammonium hydroxide, ammonium carbonate, ammonium bicarbonate, a tetraalkylammonium hydroxide or an organic amine so as to form a precipitate, the cobalt, zinc and precipitant being brought together at a rate such that a substantially constant pH in the range from 6 to 9 is maintained, and (II') recovering the precipitate so-obtained.

Steps (I') and (II') may be effected either batchwise or continuously.

Step (I') of the aforesaid process may suitably be accomplished by continuously feeding simultaneously to a precipitation zone and mixing therein a solution of a soluble compound of cobalt and zinc and a solution of the precipitant, the solution of the precipitant being fed at such a rate as to maintain the pH of the mixture substantially constant within the range from 6 to 9. The precipitation zone may suitably take the form of a vessel provided with means for separately introducing a solution of a soluble compound of cobalt and zinc and a solution of the precipitant so arranged as to mix the solutions, agitation means, pH measuring means and means for continuously withdrawing the precipitate, for example an overflow pipe. Instead of the solution of the precipitant a solid precipitant may be employed.

Continous operation in the manner of step (I') and (II') facilitates the production of the composition on a commercial scale.

Any soluble salt of cobalt and zinc may be employed. Suitable salts include, for example, carboxylates, chlorides and nitrates. In contrast with impregnation methods, chlorides are equally effective in precipitation methods for preparing the catalyst.

It is preferred to use aqueous solutions of the salts, though aqueous alcoholic solutions for example may be employed if desired.

As regards the precipitant, in addition to ammonium carbonate, ammonium bicarbonate and ammonium hydroxide, tetraalkylammonium hydroxides and organic amines may also be used. The alkyl group of the tetraalkylammonium hydroxide may suitably be a $C_1$ to $C_4$ alkyl group. A suitable organic amine is cyclohexylamine. Experiments have shown that the use of alkali metal precipitants lead to very much inferior catalysts. It is therefore preferred to avoid the presence of alkali metals in the catalyst composition. Compositions free from alkali metal may suitably be produced using as the precipitant either ammonium carbonate or ammonium bicarbonate, even more preferably ammonium bicarbonate. Ammonium carbonate may suitably be used in a commercially available form, which comprises a mixture of ammonium bicarbonate and ammonium carbamate. Instead of using a pre-formed carbonate or bicarbonate it is possible to use the precursors of these salts, for example a soluble salt and carbon dioxide.

Precipitation whether it be under rising pH or constant pH conditions is preferably carried out at a temperature below 50° C., even more preferably at a temperature below 30° C. It will usually be found convenient to operate at room temperature, for example 15° to 25° C.

Step (I) or Step (I') may be carried out in an atmosphere of carbon dioxide.

In step (II) of the process the precipitate obtained in step (I) is recovered. This may suitably be accomplished by filtration but other methods for separating solids from liquids, for example centrifugation, may be employed. After recovery, it is preferred to wash the precipitate, suitably with water, so as to remove unwanted residual soluble matter. Thereafter, the precipitate may be dried, suitably at an elevated temperature below 200° C., for example about 150° C.

Additional metals may also be introduced, if desired, at any stage in the production of the composition, for example during the precipitation step or by post-impregnation.

Irrespective of whether the composition is prepared by impregnation, precipitation or coprecipitation or by any other method, it is preferred to carry out one or more additional steps before the composition is used as a catalyst. Thus it is preferred to roast the composition, suitably by heating it in, for example, a stream of gas such as nitrogen or air at a temperature suitably in the range from 250° to 600° C. In this manner the composition may be converted into a composition of the formula (I).

It is also necessary to reductively activate the composition, suitably by contact at elevated temperature with a reducing gas, for example hydrogen, which may be diluted with nitrogen. Typically, the conditions employed during the reductive activation step may suitably be a pressure in the range from 1 to 100 bar and a temperature in the range from 150° to 500° C. for period of up to 24 hours or longer. Whilst it is preferred to effect the reductive activation step as a discrete step prior to use as a catalyst for the conversion of synthesis gas, it may be incorporated into the synthesis gas conversion process.

In another aspect the present invention also provides a process for the conversion of synthesis gas to hydrocarbons which process comprises contacting synthesis gas under conditions of elevated temperature and atmospheric or elevated pressure with a reductively activated catalyst composition as hereinbefore described.

As is well known in the art synthesis gas principally comprises carbon monoxide and hydrogen and possibly also minor amounts of carbon dioxide, nitrogen and other inert gases depending upon its origin and degree of purity. Methods of preparing synthesis gas are established in the art and usually involve the partial oxidation of a carbonaceous substance, e.g. coal. Alternatively, synthesis gas may be prepared, for example by the catalytic steam reforming of methane. For the purpose of the present invention the carbon monoxide to hydrogen ratio may suitably be in the range from 2:1 to 1:6. Whilst the ratio of the carbon monoxide to hydrogen in the synthesis gas produced by the aforesaid processes may differ from these ranges, it may be altered appropriately by the addition of either carbon monoxide or hydrogen, or may be adjusted by the so-called shift reaction well known to those skilled in the art.

The elevated temperature may suitably be in the range from 160° to 350° C., preferably from 200° to 250° C. The pressure may suitably be in the range from 0 to 100 bar, preferably from 10 to 50 bar. The GHSV for continuous operation may suitably be in the range from 100 to 25000 $h^{-1}$.

The process may be carried out batchwise or continuously in a fixed bed, fluidised bed or slurry phase reactor.

It is an advantage of the process of the present invention that it can be operated in a manner whereby the carbon dioxide make is low and, unexpectedly in view of the nature of the catalyst, the oxygenates make is very low. Surprisingly also, the process can be very selective to hydrocarbons in the $C_5$-$C_{60}$ range and particularly to wax range hydrocarbons. In contrast it has been observed that similarly prepared ruthenium/zinc oxide catalysts are almost inactive and iron/zinc oxide catalysts produce very light hydrocarbons in low selectivities. The catalyst composition of the present invention therefore provides a route to gasoline range hydrocarbons involving the production of wax range hydrocarbons and subsequent cracking and upgrading of this product.

In a modification of the process of the present invention the catalyst of formula (I) may incorporate a suitable porometallotectosilicate. The porometallotectosilicate may suitably be an aluminosilicate zeolite, preferably an aluminosilicate zeolite having a high (that is greater than 10:1) silica to alumina ratio. Suitable aluminosilicate zeolites include, but are by no means restricted to zeolite MFI-type, as described in for example U.S. Pat. No. 3,702,886.

In a further more preferred modification, the process of the invention may include a further step in which the product, or at least a portion thereof, obtained by contacting synthesis gas with the catalyst of formula (I) is up-graded by, for example, oligomerisation of lower olefins present therein to higher hydrocarbons in the manner described in, for example, U.S. Pat. Nos. 4,544,792, 4,520,215 and 4,504,693; hydrocracking in the manner described in, for example GB-A-2,146,350; cracking and isomerisation of heavy by-products in the manner described in, for example, U.S. Pat. No. 4,423,265 and up-grading in the manner described in, for example AU-A-8,321,809 and GB-A-2,021,145.

The invention will now be further illustrated by the following Examples. In the Examples CO conversion is defined as moles of CO used/moles of CO fed × 100 and carbon selectivity as moles of CO attributed to a particular product/moles of CO converted × 100.

EXAMPLE 1

Co:Zn = 1:2

A. Catalyst Preparation

Ammonium bicarbonate (215 g, 2.72 mol) was dissolved in distilled water (2 $dm^3$) and stirred vigorously at room temperature. To this solution was added a solution containing Cobaltous nitrate (50.0 g, 0.17 mol) and zinc nitrate (102.2 g, 0.34 mol) dissolved in 1 $dm^3$ of distilled water. The rate of addition of the metal salts solution was approximately 12 $cm^3$/min. The pH of the bicarbonate solution remained reasonably constant during the addition (ca pH 7.5–8.0). The resulting fine precipitate remained suspended in the stirred solution throughout the addition period. The precipitate was collected and dried on a filter bed.

Residual matter was washed from the precipitated cake by suspending it in 500 $cm^3$ of distilled water, stirring the suspension vigorously and again filtering to dryness. The washing procedure was repeated a second time before the precipitated cake was dried in an oven at 150° C. for 16 hours.

B. Catalyst Pretreatment

The oven dried cake was heated under an atmosphere of flowing nitrogen and then hydrogen according to the following temperature programme:

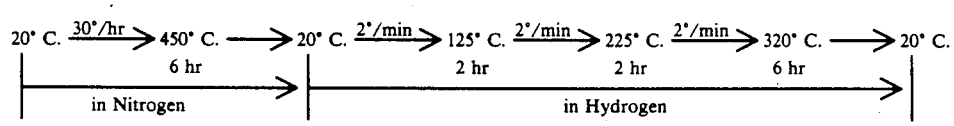

The resulting catalyst was opened to air before storing in a bottle.

C. Catalyst Testing

The catalyst was pressed to 6 tons and the resulting pellets crushed and sieved to BSS 18-25 mesh. It was mixed with an equal volume of carborundum (BSS 18-25 mesh) and loaded into a fixed bed reactor. A stream of hydrogen was passed over the catalyst bed which was given the following overnight heating programme:

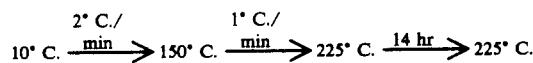

The bed temperature was reduced to 170° C. before introducing syngas ($H_2/CO=2$) and pressurising to 30 bar. The syngas flow rate was adjusted to give the required bed GHSV and the temperature was increased until syngas conversion occurred.

EXAMPLE 2

Co:Zn=1:1

The method used in Example 1 was repeated except that 75.0 g (0.25 mol) of cobaltous nitrate, 76.7 g (0.25 mol) of zinc nitrate and 270 g (3.42 mol) of ammonium bicarbonate were used.

EXAMPLE 3

Co:Zn=2:1

The method used in Example 1 was repeated except that 100 g (0.34 mol) of cobaltous nitrate, 51.1 g (0.17 mol) of zinc nitrate and 270 g (3.42 mol) of ammonium bicarbonate were used.

EXAMPLE 4

Co:Zn=1:3

The method used in Example 1 was repeated except that 37.5 g (0.13 mol) of cobaltous nitrate and 115.0 g (0.39 mol) of zinc nitrate were used.

EXAMPLE 5

Co:Zn=1:4

The method used in Example 1 was repeated except that 30.0 g (0.10 mol) of cobaltous nitrate and 122.6 g (0.41 mol) of zinc nitrate were used.

EXAMPLE 6

Co:Zn=1:5

The method used in Example 1 was repeated except that 25.0 g (0.086 mol) of cobaltous nitrate, 127.8 g (0.43 mol) of zinc nitrate and 235 g (2.97 mol) of ammonium bicarbonate were used.

EXAMPLE 7

Co:Zn=1:2 from cobaltous chloride

The method used in Example 1 was repeated except that 40.9 g (0.17 mol) of cobaltous chloride and 102.2 g (0.34 mol) of zinc nitrate were dissolved in 0.75 dm$^3$ of distilled water. The base solution contained 300 g (3.80 mol) of ammonium bicarbonate dissolved in 2 dm$^3$ of distilled water.

EXAMPLE 8

Co:Zn=1:2 from cobaltous acetate

The method used in Example 1 was repeated except that 42.8 g (0.17 mol) of cobaltous acetate and 102.2 g (0.34 ml) of zinc nitrate were dissolved in 0.75 dm$^3$ of distilled water. The base solution contained 300 g (3.80 mol) of ammonium bicarbonate dissolved in 2 dm$^3$ of distilled water.

EXAMPLE 9

Co:Zn=1:2 precipitated by Cyclohexylamine

The method used in Example 1 was repeated except that 50.0 g (0.17 mol) of cobaltous nitrate and 102.2 g (0.34 mol) of zinc nitrate were dissolved in 0.75 dm$^3$ of distilled water. The base solution contained 418 g (4.31 mol) of cyclohexylamine mixed with 2.5 dm$^3$ distilled water.

EXAMPLE 10

Co:Zn:Cr=4:7:1

The method used in Example 1 was repeated except that 17.2 g (0.04 mol) of chromium (III) nitrate was added to a solution already containing 50.0 g (0.17 mol) of cobaltous nitrate and 89.25 g (0.30 mol) of zinc nitrate dissolved in 0.75 dm$^3$ of distilled water. The base solution contained 450 g (5.70 mol) of ammonium bicarbonate dissolved in 3 dm$^3$ of distilled water.

EXAMPLE 11

Co:Zn:Zr=4:7:1

The method used in Example 1 was repeated except that 12.22 g (0.04 mol) of zirconyl nitrate was added to a solution already containing 50.0 g (0.17 mol) of cobaltous nitrate and 89.25 g (0.30 mol) of zinc nitrate dissolved in 1.0 dm$^3$ of distilled water. The base solution contained 330 g (4.18 mol) of ammonium bicarbonate dissolved in 2 dm$^3$ of distilled water.

EXAMPLE 12

Co:Zn:Ga=4:7:1

The method used in Example 1 was repeated except that 15.59 g (0.04 mol) of gallium nitrate was added to a solution already containing 50.0 g (0.17 mol) of cobaltous nitrate and 89.25 g (0.30 mol) of zinc nitrate dissolved in 0.75 dm$^3$ of distilled water. The base solution contained 450 g (5.70 mol) of ammonium bicarbonate dissolved in 3 dm$^3$ of distilled water.

EXAMPLE 13

Co:Zn:Ru=1:2:0.0054

The method used in Example 1 was repeated except that 0.244 g (0.92 mmol) of ruthenium chloride was added to a solution already containing 50.0 g (0.17 mol) of cobaltous nitrate and 102.2 g (0.34 mol) of zinc nitrate dissolved in 0.75 dm$^3$ of distilled water. The base solution contained 450 g (5.70 mol) of ammonium bicarbonate dissolved in 3 dm$^3$ of distilled water.

EXAMPLE 14

Co:Zn=1:4 by continuous coprecipitation

Ammonium bicarbonate (770 g, 9.75 mol) was dissolved in 7 dm$^3$ of distilled water. A second solution was prepared by dissolving cobaltous nitrate (85.7 g, 0.29 mol) and zinc nitrate (350.0 g, 1.16 mol) in 2.86 dm$^3$ of distilled water. These solutions were separately pumped into a stirred reactor vessel (500 cm$^3$) where precipitation occurred. The rate of addition of the nitrate and bicarbonate solutions was 32 and 83 cm$^3$/minute respectively. The resulting precipitate/slurry was pumped out of the reactor vessel at a rate of 115 cm$^3$/min directly onto a filter bed. The pH in the precipitation vessel remained between 7.35 and 7.40 during the addition period (90 minutes). The precipitated cake was washed free of residual matter by suspending it in 2 dm$^3$ of distilled water which was vigorously stirred. The resulting suspension was then filtered to dryness. The washing procedure was repeated a second time before the precipitated cake was dried in an oven at 150° C. for 16 hours. The catalyst was given the same pretreatment as described in Example 1.

EXAMPLE 15

Co:Zn = 1:15 by impregnation

Cobaltous nitrate (18.3 g, 62 mmol) was dissolved in 80 cm$^3$ of AnalaR acetone. This solution was slowly added to ZnO (70 g) with continuous stirring until a consistent paste was formed. A further 20 cm$^3$ of acetone was used to ensure that all of the cobalt was washed onto the zinc oxide. With continuous stirring/kneading, the paste was dried over a steam bath until a uniform powder was formed. The powder was left in an oven at 150° C. overnight. The catalyst was given the same pretreatment as described in Example 1.

EXAMPLE 16

Co:Zn = 1:2 tested with zeolite H-MFI

The method used in Example 1 was repeated and 5 cm$^3$ of the finished catalyst (BSS 18–25 mesh) was mixed with 5 cm$^3$ of carborundum (BSS 18–25 mesh). This was loaded into a fixed-bed reactor with a further 7 cm$^3$ of carborundum loaded downstream of the FT bed. A bed of H-MFI zeolite (10 cm$^3$, BSS 18–25 mesh) was then postioned downstream of both the FT bed and carborundum spacer. A temperature of 233° C. was applied to the FT bed and 321° C. to the zeolite bed. The waxy hydrocarbon product, CO$_2$ and water from the FT bed, along with unreacted synthesis gas, were all fed over the zeolite. The wax product was upgraded to LPG and a liquid C$_5$+ product.

The results of Examples 1 to 16 are given in the accompanying Table.

TABLE

Results for Syngas to Hydrocarbon Conversion
H$_2$:CO = 2:1
Pressure = 30 bar

| Example | T/°C. | Bed GHSV | % CO Conversion | % Carbon Molar Selectivity | | | | |
|---|---|---|---|---|---|---|---|---|
| | | | | CO$_2$ | CH$_4$ | C$_3$+ | C$_5$+ | oxygenates |
| 1 | 216 | 2500 | 64.2 | 0.5 | 9.1 | 89.6 | 87.7 | 0.1 |
| 1 | 206 | 1250 | 70.1 | 0.5 | 8.3 | 90.5 | 89.0 | 0.1 |
| 2 | 240 | 2500 | 68.0 | 2.8 | 20.5 | 74.1 | 70.6 | 0.4 |
| 3 | 216 | 2500 | 53.9 | 1.6 | 12.8 | 83.1 | 78.8 | 0.4 |
| 4 | 252 | 1500 | 56.2 | 2.0 | 19.3 | 75.9 | 70.0 | 0.4 |
| 5 | 232 | 2500 | 60.7 | 1.2 | 16.2 | 81.2 | 78.2 | 0.1 |
| 6 | 259 | 2500 | 55.2 | 2.6 | 27.6 | 66.6 | 59.3 | 0.2 |
| 7 | 246 | 2500 | 60.9 | 1.2 | 14.6 | 82.0 | 75.5 | 0.8 |
| 8 | 240 | 2500 | 52.7 | 1.2 | 14.1 | 82.7 | 78.1 | 0.7 |
| 9 | 202 | 2500 | 43.0 | 0.3 | 8.0 | 90.4 | 85.8 | 0.3 |
| 10 | 233 | 2500 | 58.1 | 1.3 | 15.5 | 81.6 | 76.9 | 0.4 |
| 11 | 218 | 2500 | 55.1 | 0.8 | 11.0 | 86.9 | 84.0 | 0.4 |
| 12 | 218 | 2500 | 48.9 | 0.6 | 15.5 | 82.2 | 77.2 | 0.4 |
| 13 | 219 | 2500 | 64.2 | 0.8 | 9.1 | 88.9 | 85.1 | 0.4 |
| 14 | 209 | 1250 | 56.5 | 0.5 | 6.3 | 91.8 | | 0.7 |
| 15 | 238 | 2500 | 42.5 | 0.9 | 18.5 | 76.9 | | 1.4 |
| 16 | 233* | 2500 | 50.6 | 1.9 | 12.1 | 84.8* | | 0.04 |
| Comp Test 1 | 325 | 2500 | 67.0 | 33.3 | 23.1 | 31.0 | | 1.4 |
| Comp Test 2 | 350 | 2500 | <5.0 | # | # | # | | # |

*FT bed at 233° C., zeolite bed at 321° C., the C$_3$+ *selectivity of 84.8% was 46.3% LPG and 38.5% of a liquid C$_5$+ product.*

*In view of the very low conversion the product was not analysed.*

COMPARISON TEST 1

Iron Catalyst Preparation

Ammonium bicarbonate (225 g, 2.85 mol) was dissolved in distilled water (2 dm$^3$) and stirred vigorously at room temperature. To this solution was added a solution containing ferric nitrate (123.6 g, 0.30 mol) and zinc nitrate (24.0 g, 0.08 mol) dissolved in 1 dm$^3$ of distilled water. The rate of addition of the metal salts solution was approximately 12 cm$^3$/min. The remainder of the preparation was the same as described for the cobalt catalyst in Example 1.

B. Catalyst Pretreatment

The procedure of Example 1 was repeated.

C. Catalyst Testing

The procedure of Example 1 was repeated.

The results are presented in the Table.

COMPARISON TEST 2

1% Ru/ZnO

A. Preparation

Ammonium bicarbonate (154 g, 1.95 mol) was dissolved in distilled water (2 dm$^3$) and stirred vigorously at room temperature. To this solution was added a solution containing ruthenium chloride (0.65 g, ca 2.5 mmol) and zinc nitrate (92.7 g, 0.31 mol) dissolved in 750 cm$^3$ of distilled water. The rate of addition of the metal salts solution was approximately 12 cm$^3$/min. The remainder of the preparation was the same as described for Example 1.

B. Catalyst Pretreatment

The procedure of Example 1 was repeated.

C. Catalyst Testing

The procedure of Example 1 was repeated.

The results are presented in the Table.

Comparison Tests 1 and 2 are not in accordance with the present invention and are included only for the purpose of comparison.

I claim:

1. A process for the conversion of a synthesis gas of carbon monoxide and hydrogen to waxy hydrocarbon which process comprises contacting synthesis gas under conditions of elevated temperature and pressure with a reductively activated catalyst composition to selectively obtain waxy hydrocarbon products, wherein said catalyst composition consists of (i) cobalt either as elemental metal, the oxide or a compound thermally decomposable to the elemental metal and/or oxide and (ii) zinc in the form of the oxide or a compound thermally decomposable to the oxide, said composition being obtained by a process comprising: (I) precipitating at a temperature in the range from 0° to 100° C. the the metals cobalt and zinc in the form of insoluble thermally decomposable compounds thereof from a solution of soluble compounds thereof using a precipitant comprising ammonium hydroxide, ammonium carbonate, ammonium bicarbonate, a tetraalkyl ammonium compound or an organic amine, and (II) recovering the precipitate obtained in step (I), the molar ratio of said soluble compounds of cobalt to zinc being in the range from 1:5 to 2:1.

2. A process according to claim 1 wherein the elevated temperature is in the range from 160° to 350° C. and the pressure is in the range from 0 to 100 bar.

3. A process according to claim 1 including the further step of up-grading the hydrocarbon product or, at least a portion thereof, by oligomerisation of lower olefins present therein to higher hydrocarbons.

4. A process according to claim 1 including the further step of hydrocracking the hydrocarbon product, or at least a portion thereof.

5. A process according to claim 1 including the further step of cracking and isomerising the hydrocarbon product, or at least a portion thereof.

* * * * *

UNITED STATES PATENT AND TRADEMARK OFFICE
CERTIFICATE OF CORRECTION

PATENT NO. : 5,023,277
DATED : June 11, 1991
INVENTOR(S) : COLIN H. McATEER

It is certified that error appears in the above-identified patent and that said Letters Patent is hereby corrected as shown below:

Col. 5, l. 17, should read "for a period".

Col. 11, claim 1, l. 20, delete the second word "the".

Signed and Sealed this

Eighth Day of December, 1992

Attest:

DOUGLAS B. COMER

Attesting Officer

Acting Commissioner of Patents and Trademarks